United States Patent [19]
Miura et al.

[11] Patent Number: 5,780,865
[45] Date of Patent: Jul. 14, 1998

[54] APPARATUS FOR DETECTING IMAGES OF PARTICULATES IN LIQUID

[75] Inventors: Ryosuke Miura, Tokyo-to; Kiyoshi Taguchi, Sapporo; Kazuyuki Ito, Tokyo-to, all of Japan

[73] Assignee: Kabushiki Kaisha Toshiba, Kawasaki, Japan

[21] Appl. No.: 694,783

[22] Filed: Aug. 9, 1996

[30] Foreign Application Priority Data

Aug. 11, 1995 [JP] Japan .................................. 7-205772

[51] Int. Cl.⁶ .................................................. G01N 15/06
[52] U.S. Cl. .............................. 250/573; 250/576; 356/442
[58] Field of Search ................................ 250/573, 574, 250/575, 576; 356/442, 335, 336

[56] References Cited

U.S. PATENT DOCUMENTS

5,166,537  11/1992  Horiuchi et al. ................ 250/573
5,194,921  3/1993  Tambo et al. .................... 356/442

*Primary Examiner*—Edward P. Westin
*Assistant Examiner*—Kevin Pyo
*Attorney, Agent, or Firm*—Foley & Lardner

[57] ABSTRACT

An imaging glass window and an illumination glass window which are opposed to each other define a sample chamber, and the sample chamber holds sample liquid containing particulates. Light from the particulates is magnified by a zoom magnifying glass via the imaging glass window, optical axis angle changing means and optical axis length changing means and imaged by a CCD camera. An image of the sample liquid is supplied to image control means, and the optical axis angle changing means is operated by the image control means to change an optical axis of the light from the sample liquid and shift an image of an intended one of the particulates in the sample liquid to the center a camera lens of the cameraeen. Concurrently the zoom magnifying glass is set at a required magnification by the control means.

10 Claims, 7 Drawing Sheets

(LOW MAGNIFICATION)

FIG.6B

(HIGH MAGNIFICATION)

ADJUSTING OF OPTICAL AXIS OF LIGHT (HIGH MAGNIFICATION)

APPARATUS FOR DETECTING IMAGES OF PARTICULATES IN LIQUID

FIELD OF INDUSTRIAL APPLICATION

The present invention relates to an apparatus for detecting images of particulates in liquid which can detect clear images of particulates in liquid irrespective of their sizes to analyze characteristics of the particulates suspending in liquid.

PRIOR ART

Insects, plants and minerals, etc. suspend and float in liquid, especially in rivers, lakes and swamps, seas, water purifying plants, processing water of swage-treatment plants and pigment production, etc. Shapes of these insects, plants, minerals are detected by physico-chemical analyzing devices which have been conventionally widely automated but still have much significant information left undetected. But these suspended particulates are too fine to be detected by means other than the so-called microscopes. In addition, the suspended particulates have various large and small sizes. Smaller ones of the particulates are detected vaguely by a microscope of a fixed magnification, and larger ones of the particulates cannot be completely covered by the view field and cannot be imaged.

As means for imaging complete particulates of various large and small sizes in water, a plurality of magnifying glasses of different magnifications are prepared, and the magnifications are changed to select a suitable magnification.

When finer particulates are magnified to be imaged by replacing a magnifying glass by that of a higher magnification, it is necessary that the particulates are in the magnified image. In such case, the conventional technique, however, cannot image particulates when a magnification of the magnifying glasses is increased.

SUMMARY OF THE INVENTION

In view of the above-described point the present invention was made, and an object of the present invention is to provide an apparatus for detecting images of particulates in liquid which can magnify and image finer ones of the particulates in liquid to accurately grasp their complete images.

The present invention relates to an apparatus for detecting images of particulates in liquid comprising a sample chamber defined by a pair of opposed glass windows, for holding sample liquid containing particulates, a zoom magnifying glass disposed adjacent to one of the glass windows and having variable magnifications, a camera having a camera lens disposed adjacent to the zoom magnifying glass, for receiving light from the sample liquid via the zoom magnifying glass and producing image information of the sample liquid, an optical path angle changing means disposed between the sample chamber and the zoom magnifying glass, for changing an optical path of the light from the sample liquid, and image control means for, based on the image information of the sample liquid from the camera, controlling the optical path angle changing means so that an image of a particulate in the sample liquid is shifted to the center of the camera lens, and setting the zoom magnifying glass at a required magnification.

According to the present invention, the light from sample liquid containing particulates, which is held in the sample chamber passes through one of the window glasses and the optical axis angle changing means, and is magnified by the zoom magnifying glass and imaged by the camera. An image of the sample liquid is supplied from the camera to the image control means, and the optical axis angle changing means is controlled by the image control means, so that an optical axis of the light from the sample liquid is changed to shift an image of an intended one of the particulates to the center of the camera lens. Concurrently the zoom magnifying glass is set at a required magnification by the image control means. Thus, the image of the particulate is shifted to the center of the camera lens to thereby accurately completely grasp the image of the intended particulate.

EMBODIMENTS

An embodiment of the present invention will be explained with reference to the drawings. FIGS. 1 to 7 are views of an apparatus for detecting images of particulates in liquid according to one embodiment of the present invention.

Figure 1:
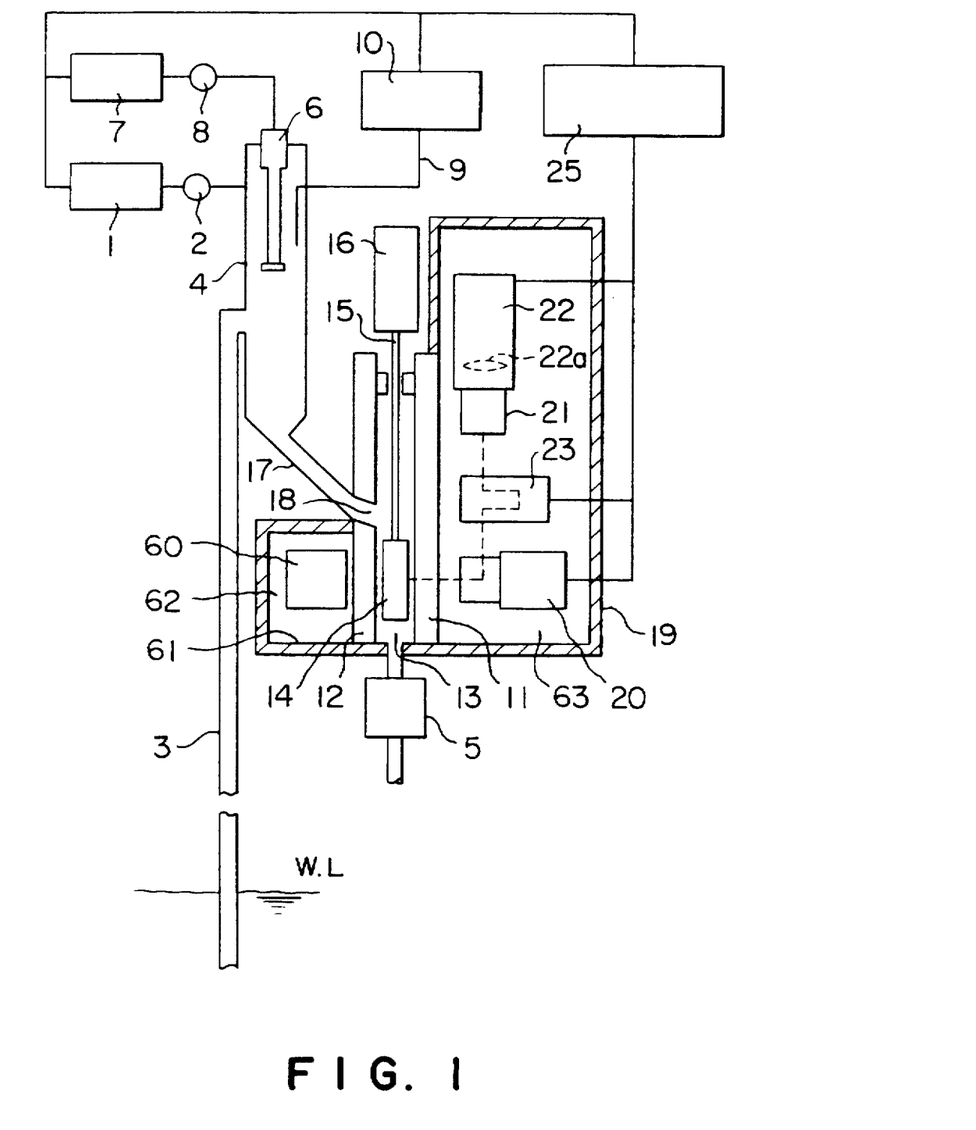
FIG. 1 is a block diagram of the device for detecting images of particulates in liquid according to one embodiment of the present invention.

In FIG. 1, the apparatus for detecting images of particulates in liquid comprises a main case 19, and a projection glass window 11 and an illumination glass window 12 opposed to each other in the main case 19. The projection glass window 11 and the illumination glass window 12 define a sample chamber 13 into which sample liquid containing fine particulates is caused to flow. A drain valve 5 is provided below the sample chamber 13.

The sample chamber 13 is connected to a tank 4 through a feed pipe 17 having an opening 18, and the tank is fed with sample liquid through a sample liquid feed pipe 3.

A purging means 6 which cleans the interior of the tank 4 is disposed in the tank 4, and an air pump 1 is connected to the interior of the tank 4 through an air valve 2. The purging means 6 in the tank 4 is connected to a purging liquid feed pump 7 through a purging liquid feed valve 8, and the tank 4 is connected to agent feed means 10 through an agent feed pipe 9. The purging means 6 and the purging liquid fed pump 7 are for cleaning the interior of the tank, and the air pump 1 is for sacking sample liquid into the tank 4.

A slide glass 14 is disposed vertically movably in the sample chamber 13. The slide glass 14 is moved by an actuator 16 through a shaft 15.

As shown in FIG. 1, an illumination chamber 62 is defined by the illumination glass window 12 on the left side in the interior of the main case 19, and a light source 60 is housed in the illumination chamber 62. On the part of the inside wall of the illumination chamber 62 except the illumination glass window 12 there is provided a reflecting mirror 61 which reflects light of the light source 60 toward the sample chamber 13.

On the other hand, an imaging chamber 63 is defined by the projection glass window 11 on the right side in the interior of the main case 19. There are disposed an optical path angle changing means 20 which changes the optical path of light, an optical path length changing means 23, and a CCD camera 22 including a camera lens 22a with a zoom magnifying glass 21 in the imaging chamber 63 upwardly from the side of the sample chamber 13 in the above stated order. The optical path angle changing means 20, the optical path length changing means 23 and the CCD camera 22 are connected to control means 25. The control means 25 controls the air pump 1, the air valve 2, the purging liquid feed pump 7 and the purging liquid feed valve 8 and the agent feed means 10.

Figure 2A:
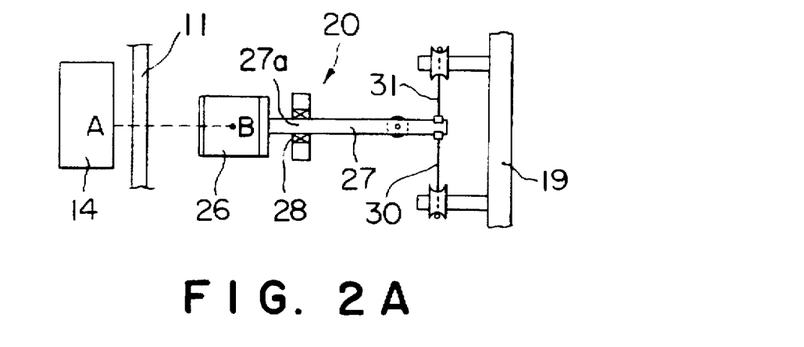
FIG. 2A is a plan view showing an optical path angle changing means, which explains a structure thereof.

Then optical path angle changing means 20 will be detailed with reference to FIGS. 2A to 2C. FIG. 2A is a plan view of the optical path angle changing means 20, FIG. 2B is a side view of the optical path angle changing means 20, and FIG. 2C is a view of the side view of FIG. 2B as viewed in the direction of the arrow X.

Figure 2B:
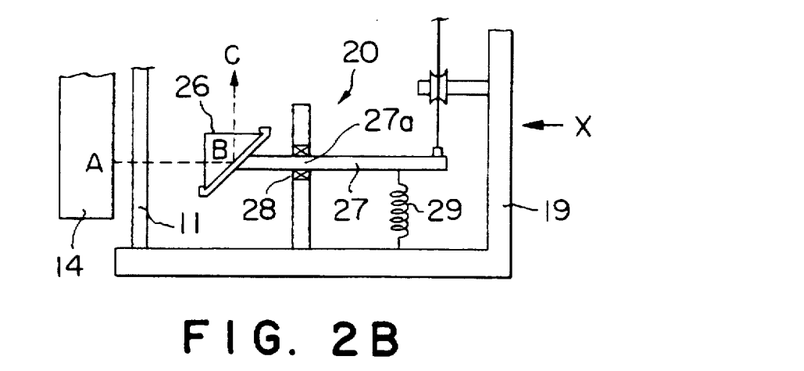
FIG. 2B is a side view showing the optical path angle changing means, which explains the structure thereof.
Figure 2C:
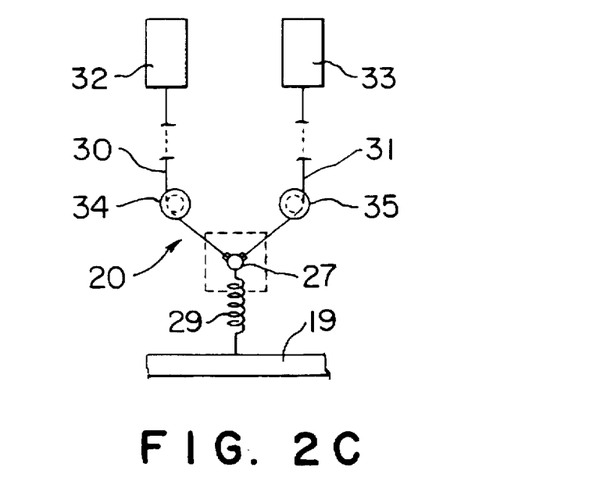
FIG. 2C is a view of FIG. 2B as viewed in the direction of the arrow X.

As shown in FIGS. 2A to 2C, the optical path angle changing means 20 includes a prism 26, and light of sample liquid which is in an area between the imaging glass window 11 and the slide glass 14 goes from a portion A, and then is reflected at the point B of the prism 26 in the direction C toward the CCD camera 22. The prism 26 is secured to one end of a shaft 27 disposed substantially horizontal, and the shaft 27 is swingable on the middle part 27a thereof supported by a ball bearing 28 as the fulcrum. The shaft 27 has an opposed portion to the prism 26 connected to the main case 19 by a spring 29, and the other end of the shaft 27 is connected to wires 30, 31. As shown in FIG. 2C, the wires 30, 31 intersect each other at about 90°. The wires 30, 31 are connected to respective X-axis hoist means 32 and a Y-axis hoist means 33 respectively through pulleys 34, 35.

Then the optical path length changing means 23 will be detailed with reference to FIGS. 3A to 3C.

Figure 3A:
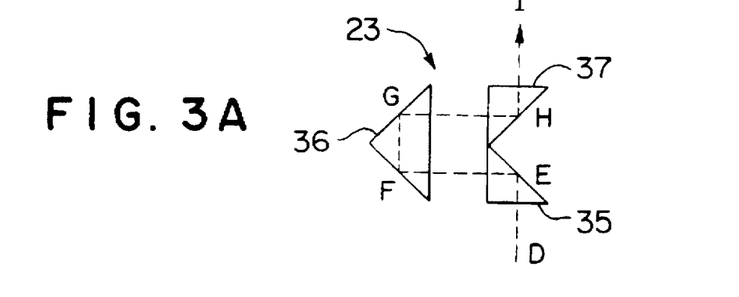
FIG. 3A is a side view showing the optical path length changing means, which explains a principle thereof
Figure 3B:
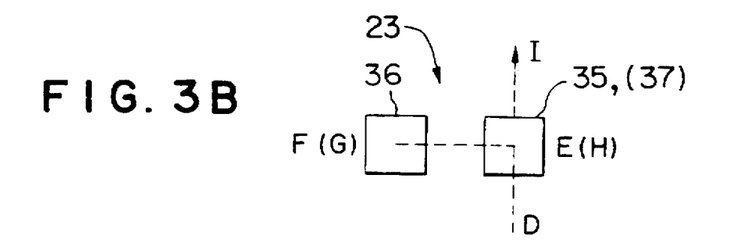
FIG. 3B is a plan view showing the optical path length changing means, which explains the principle thereof.

FIGS. 3A and 3B are explanatory views showing the principle of the optical path length changing means 23. FIG. 3C is a detailed view of the optical path length changing means 23. As shown in FIGS. 3A to 3C, light from the sample liquid is incident in a direction D to the point E of a stationary prism 35 and is reflected normally at the point E. Then the light is reflected at the points F and G of a movable prism 36 toward the point H of the stationary prism 37 and then goes in a direction I to the zoom magnifying glass 21. In this way, the optical path length from the point E to the point H can be longer by a total of a distance EF and a distance GH. Accordingly the optical path length can be adjusted, by moving the movable prism 36 to and away from the a pair of opposed stationary prisms 35, 37 to change a total of the distances EF and GH.

Figure 3C:
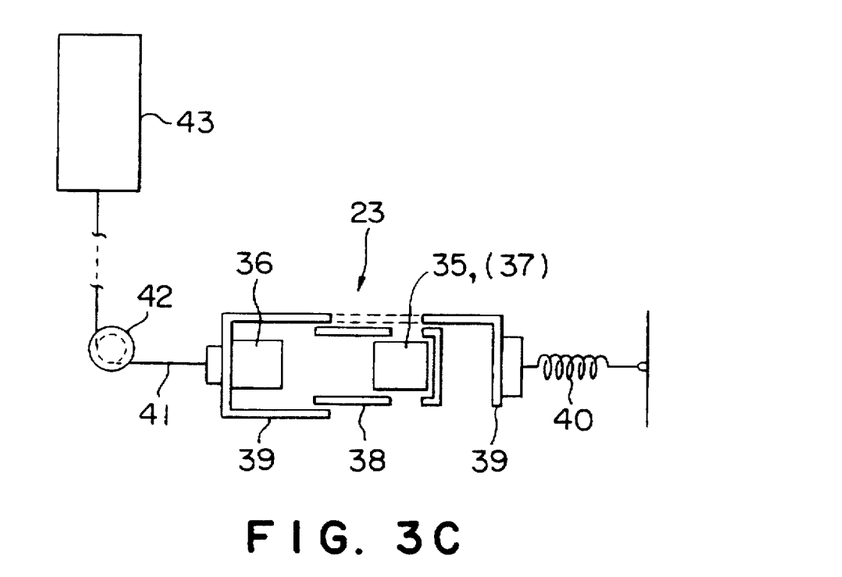
FIG. 3C is a view showing the optical path length changing means, which explains a structure thereof.

As shown in FIG. 3C, the optical path length changing means 23 includes the prisms 35, 36, 37. The prisms 35, 37 are housed in a case 38, and the prism 36 is housed in a case 39. As shown in FIG. 3C, the case 39 is slidable along the outside the case 38. The case 30 has one end fixed through a spring 40 and the other end connected to a hoist means 43 through a wire 41 and a pulley 42.

Figure 4A:
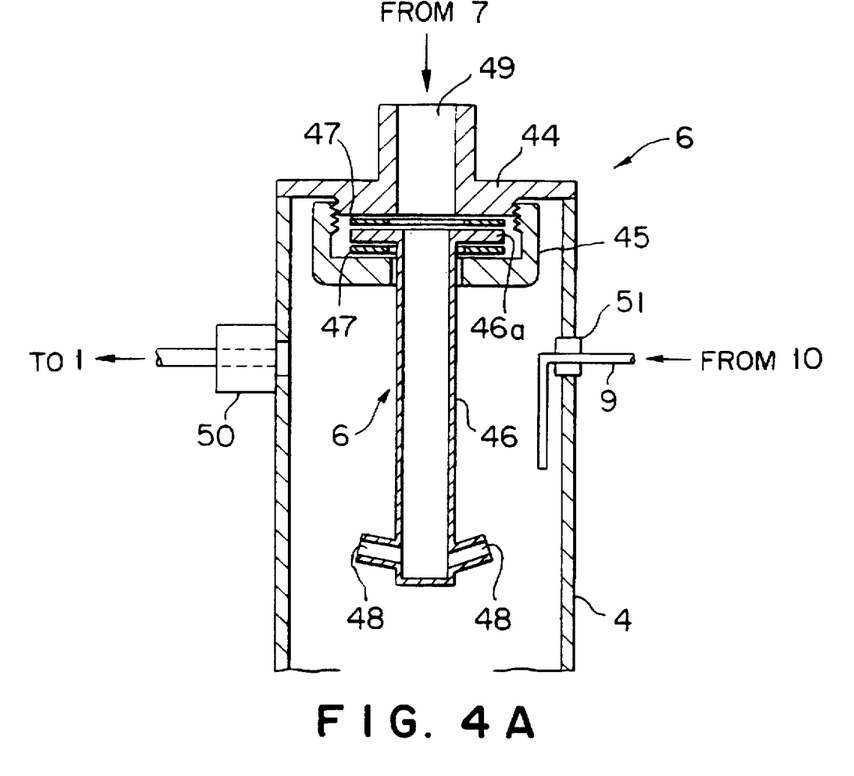
FIG. 4A is a view showing purging means, which explains a structure thereof.
Figure 4B:
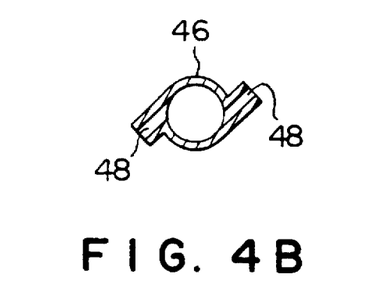
FIG. 4B is a view showing a rotary tube of the purging means.
Figure 5:
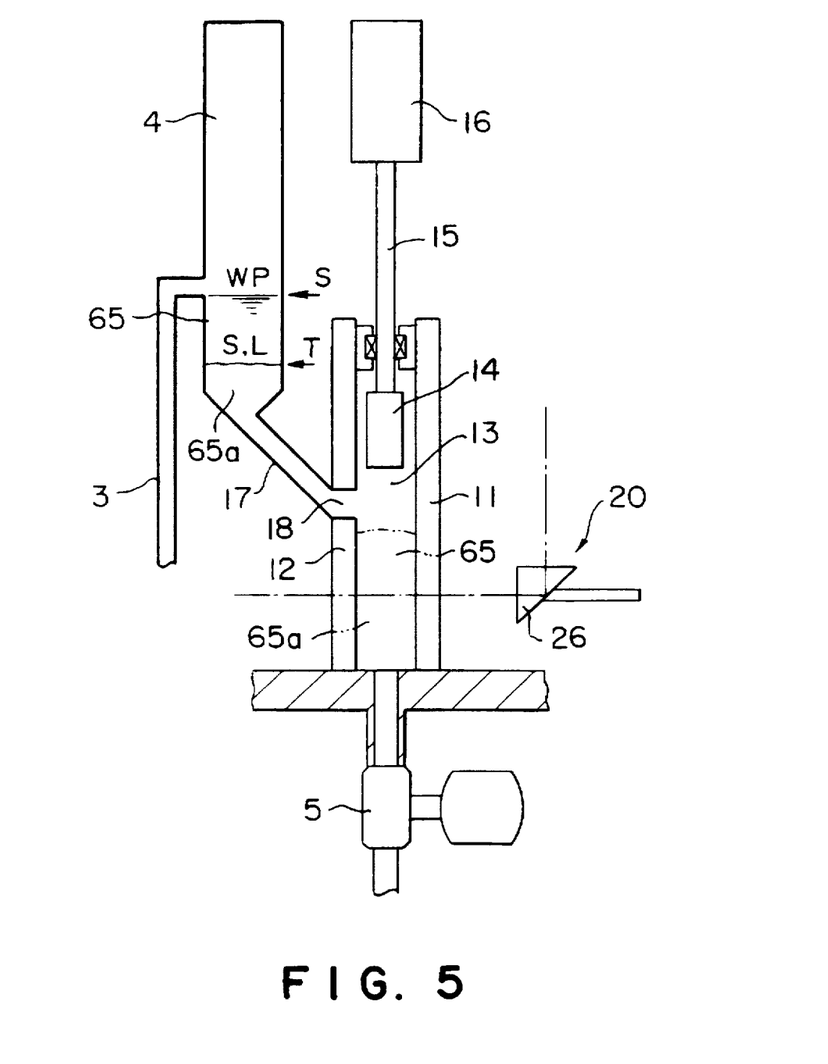
FIG. 5 is a view showing a concentration state of particulates in liquid, which explains the operation of the present invention.

The purging means 6 disposed in the tank 4 will be explained with reference to FIGS. 4A and 4B. As shown in FIGS. 4A and 4B, the purging means 6 includes a rotary tube 46 having a flange 46a. An upper lid of the tank 4 has an external screw formed in a lower part thereof, and the internal screw of a cap 45 meshes with the external screw to loosely hold the flange 46a of the rotary tube 46 through two sheets of Teflon rings 47. A pair of nozzles 48 is provided in the lower end of the rotary tube 46, and the respective nozzles 48 are extended in a circumferential direction of the rotary tube 46. When purging liquid is fed from the purging liquid feed pump 7 through an inlet port 49 in the upper lid 44, flows through the rotary tube 46 and injected through a pair of nozzles 48, the rotary tube 46 is rotated, and the purging liquid injected through the nozzles 48 cleans the inside wall of the tank 4. The tank 4 has an outlet port 50 communicated with the side of the air pump 1. The tank 4 has a mounting hole 51 for the reagent feed pipe 9.

Next, the operation of the present embodiment having the above-described structure will be explained. First, the air pump 1 is actuated with, as shown in FIG. 1, the drain valve 5 below the sample chamber 13 closed and the air valve 2 opened. At this time, the tank 4 has a lower pressure, and sample liquid 65 containing fine particulates 65a flows into the tank 4 through the sample liquid feed pipe 3. The air pump 1 is stopped, when a liquid level of the sample liquid 65 in the tank 4 is above the point S as shown n FIG. 5, and then the air valve 2 is opened to the outside. After that, air flows into the tank 4.

At this time, excessive sample liquid 65 flows oppositely through the sample liquid feed pipe 3 to be discharged. The liquid level of the sample liquid 65 is lowered to the point S. Here the sample liquid is let to stand for a required period of time. The particulates 65a in the sample liquid 65 in the tank 4 sediment and concentrate sufficiently to have a surface at the point T (see the solid line in FIG. 5). Meantime the slide glass 14 in the sample chamber 13 between the illumination glass window 12 and the imaging glass window 11 is positioned upper than the opening 18 of the feed pipe 17. Then, the drain valve 5 is opened for a set period of time, and the sufficiently concentrated sample liquid 65 flows into the sample chamber 13 through the feed pipe 17 (the two-dot chain line in FIG. 5).

Then, the slide glass 14 is gently lowered to thereby form the so-called preparation between the slide glass 14 and the imaging glass window 11. The sample liquid 65 in the thus formed preparation is imaged by the CCD camera 22 through the optical axis angle changing means 20, the optical axis length changing means 22 and the zoom magnifying glass 21. The operation of the air pump 1 and the air valve 2, and the opening/closing of the drain valve 5 are performed in response to commands of the control means 25.

Then the operation of imaging the sample liquid 65 by CCD camera 22 will be detailed. First, light from the light source 60 in the illumination chamber 62 is condensed by the reflecting mirror 61, and enters the sample chamber 13 through the illumination glass window 12 and illuminates the sample liquid 65. As described above, the light from the sample liquid 65 is imaged by the CCD camera 22 via the imaging changing means 20, and the optical axis changing means 20, the optical axis length changing means 23 and the zoom magnifying glass 21.

Figure 6A:
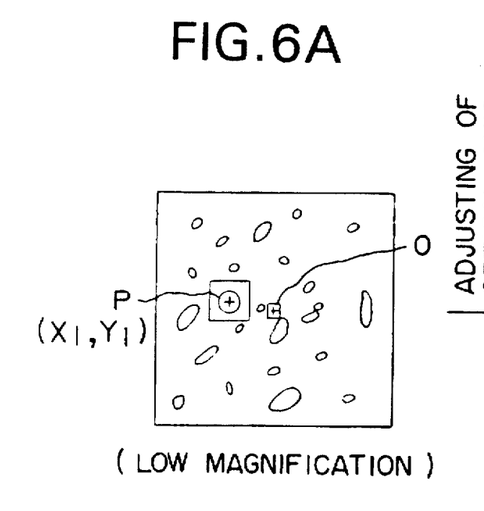
FIG. 6 is views showing images of particulates, which explain the operation of the present invention.
Figure 6B:
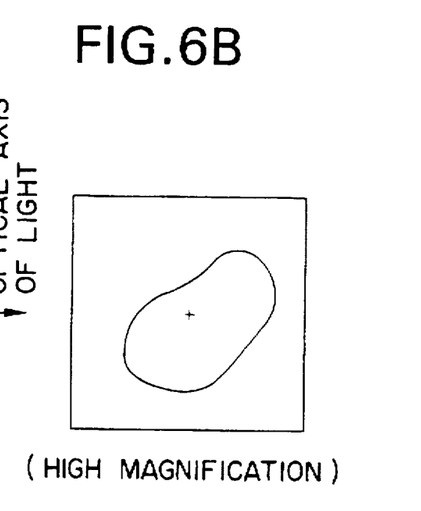
Figure 6C:
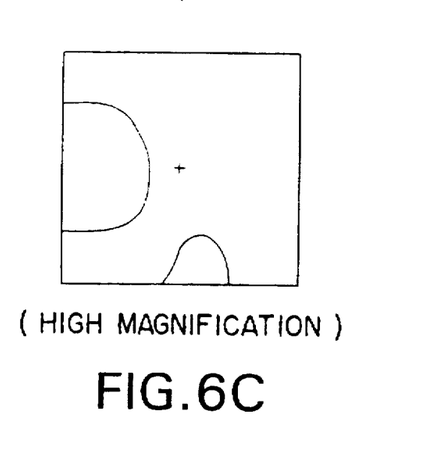

Images of the sample liquid taken by the CCD camera 22 are shown in FIGS. 6(a), (b) and (c).

FIG. 6(a) shows the image of the sample liquid when the zoom magnifying glass 21 is set at a low magnification. An optical axis O of the light from the liquid sample 65 is at the center of the screen (center of the camera lens 22a).

Figure 7:
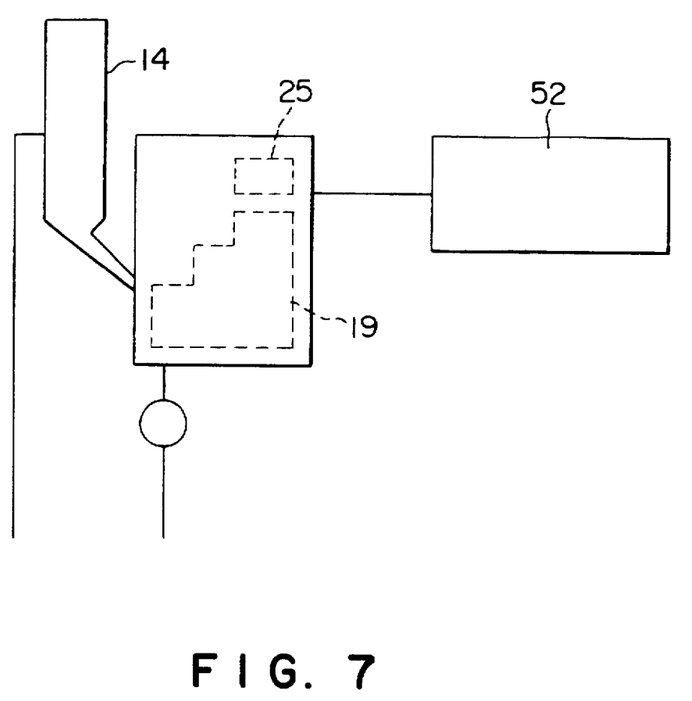
FIG. 7 is a view showing control means and image analyzing means.

As shown in FIG. 7, the sample image taken by the CCD camera 22 is supplied to the control means 25, and then is supplied from the control means 25 to an image analyzing means (personal computer) 52. In the image analyzing means 52, the sample image is processed to classify the particulates and to compute positions of the gravity centers of the respective particulates, so that that of the particulates having an intended particle size is selected. Coordinates (x1,y1) of the gravity center P of the particulate are supplied to the control means 25, and the optical path angle changing means 20 is operated by the control means 25 to displace the optical axis O of the light from the sample liquid 65 so that the gravity center P of the particulate is located at the center of the screen. Then, the magnification of the zoom magnifying glass 21 is changed to a higher magnification by the control means 25, and the sample image as shown in FIG. 6(b) can be formed. Concurrently therewith, the optical path length changing means 23 is operated by the control means 25 to adjust the optical path length of the light from the sample liquid 65, and the sample image to be formed by the CCD camera 22 is focussed.

FIG. 6(c) shows the image of the sample liquid when the zoom magnifying glass 21 is set at a high magnification without adjusting an optical axis of the light from the sample liquid 65. As shown in FIG. 6(c), a complete image of the particulate cannot be formed.

According to the present embodiment, as shown in FIG. 6(b), a particulate is shifted to the center of the screen, and a complete view of the particulate can be accurately grasped. In this case, the control means 25 and the image analyzing means 52 constitute image control means.

After such detection of the particulate image is repeated several times, the interior of the tank 4 is contaminated. The interior of the tank 4 is periodically cleaned by the control means 25. That is, after the interior of the tank 4 is emptied, the purging liquid feed pump 7 is actuated by the control means 25, and purging liquid is caused to flow into the rotary tube 46 from the purging liquid feed valve 8. Then, the purging liquid in the rotary tube 6 is discharged from the nozzles 48, and as the rotary tube 46 is rotated, the purging liquid is injected to the inside surface of the tank 4.

A required agent is poured into the sample liquid 65 in the tank from the agent feed means 10 to form clear-cut images of the particulates 65a in the sample liquid 65. It is also possible to feed from the agent feed means 10 an agent necessary to clear the interior of the tank.

As described above, according to the present invention, an image of a particulate on a sample image screen can be shifted to the center of the screen and magnified, whereby complete images of even fine particulates can be accurately grasped.

What is claimed is:

1. An apparatus for detecting images of particulates in liquid comprising:

a sample chamber defined by a pair of opposed glass windows, for holding sample liquid containing particulates;

a zoom magnifying glass disposed adjacent to one of the glass windows and having variable magnifications;

a camera having a camera lens, disposed adjacent to the zoom magnifying glass, for receiving light from the sample liquid via the zoom magnifying glass and producing image information of the sample liquid;

an optical path angle changing means disposed between the sample chamber and the zoom magnifying glass, for changing an optical path of the light from the sample liquid; and image control means for, based on the image information of the sample liquid from the camera, controlling the optical path angle changing means so that an image of a particulate in the sample liquid is shifted to the center of the camera lens, and setting the zoom magnifying glass at a required magnification.

2. The apparatus for detecting images of particulates in liquid according to claim 1, wherein the optical path angle changing means is disposed horizontal, and includes a shaft which is swung on a middle thereof as a fulcrum, a prism secured to one end of the shaft, and a pair of drive wires connected to the other end of the shaft.

3. The apparatus for detecting images of particulates in liquid according to claim 1, further comprising optical paths length changing means disposed between the sample chamber and the zoom magnifying glass, for adjusting an optical path length of the light from the sample liquid.

4. The apparatus for detecting images of particulates in liquid according to claim 3, wherein the optical path length changing means has a pair of stationary prisms opposed to each other, and a movable prism disposed movably to and from said a pair of stationary prisms.

5. The apparatus for detecting images of particulates in liquid according to claim 1, wherein a slide glass is disposed movably in the sample chamber, and the slide glass and one of the glass windows define a preparate.

6. The apparatus for detecting images of particulates in liquid according to claim 1, wherein illumination means is disposed adjacent to the other of the glass windows, and the illumination means includes a light source and a reflecting mirror.

7. The apparatus for detecting images of particulates in liquid according to claim 1, wherein a tank having suction means is connected to the sample chamber, and the tank is connected to a sample liquid feed pipe which is operated by the suction means to feed sample liquid into the tank.

8. The apparatus for detecting images of particulates in liquid according to claim 7, wherein the tank is connected to agent feed means for feeding an agent for cleaning the tank.

9. The apparatus for detecting images of particulates in liquid according to claim 7, wherein the tank is connected to agent feed means for feeding an agent for imaging the particulates clearly.

10. The apparatus for detecting images of particulates in liquid according to claim 7, wherein the tank includes purging means for purging an inside surface of the tank.

* * * * *